(12) United States Patent
Richelle et al.

(10) Patent No.: US 8,475,786 B2
(45) Date of Patent: Jul. 2, 2013

(54) LONG-LASTING ABSORPTION OF FLAVONOIDS

(75) Inventors: Myriam Richelle, Savigny (CH); Gary Williamson, Harrogate (GB); Ivana Jankovic, Epalinges (CH); Maarit Rein, Lutry (CH)

(73) Assignee: Nestec S.A., Vevey (CH)

( * ) Notice: Subject to any disclaimer, the term of this patent is extended or adjusted under 35 U.S.C. 154(b) by 858 days.

(21) Appl. No.: 12/438,501

(22) PCT Filed: Aug. 22, 2007

(86) PCT No.: PCT/EP2007/007394
§ 371 (c)(1), (2), (4) Date: Oct. 20, 2009

(87) PCT Pub. No.: WO2008/022784
PCT Pub. Date: Feb. 28, 2008

(65) Prior Publication Data
US 2010/0055081 A1    Mar. 4, 2010

(30) Foreign Application Priority Data
Aug. 24, 2006  (EP) .................................... 06017678

(51) Int. Cl.
*A01N 63/00* (2006.01)

(52) U.S. Cl.
USPC ............... 424/93.45; 435/195; 435/252.9; 514/27

(58) Field of Classification Search
None
See application file for complete search history.

(56) References Cited

U.S. PATENT DOCUMENTS

| | | | |
|---|---|---|---|
| 7,507,423 B2 * | 3/2009 | Wallace et al. | 424/725 |
| 2004/0071685 A1 | 4/2004 | Houston et al. | |
| 2004/0105849 A1 * | 6/2004 | Kaloidis | 424/93.45 |

FOREIGN PATENT DOCUMENTS

| | | | |
|---|---|---|---|
| EP | 0908524 | | 4/1999 |
| EP | 1325749 | | 7/2003 |
| JP | 2000078955 | | 3/2000 |
| JP | 2003073279 | | 3/2003 |
| WO | WO 2005/040387 | * | 5/2005 |
| WO | WO 2005058255 | | 6/2005 |
| WO | WO2008022784 | | 2/2008 |

OTHER PUBLICATIONS

Kim et al., Arch Pharm Res., 1998, vol. 21, No. 1, p. 17-23.*
Briganti et al., J Eur Deramtol Venereol, 2003, vol. 17, No. 6, p. 663-669 (Abstract only).*
Kailasapathy, K., Curr Issues Intest. Microbiol., 2002, vol. 3, p. 39-48.*
International Search Report for International Application No. PCT/EP2007/007394 mailed Sep. 11, 2008.
Written Opinion for International Application No. PCT/EP2007/007394 mailed Sep. 11, 2008.
R. Gonzalez-Barrio, et al., "Production of Bioavailable Flavonoid Glucosides in Fruit Juices and Green Tea by Use of Fungal alpha-L-Rhamnosidases," Journal of Agriculture and Food Chemistry, vol. 2152, No. 20, (2004), pp. 6136-6142.
I. Nielsen, et al., "Bioavailability Is Improved by Enzymatic Modification of the Citrus Flavonoid Hesperidin in Human: A Randomised, Double-Blind, Crossover Trial," The Journal of Nutrition, vol. 136, No. 2, Feb. 2006, pp. 404-408.
K. Oana, et al., "Physical and Genetic Map of *Enterococcus faecium* ATCC19434 and Demonstration of Intra- and Interspecific Genomic Diversity in Enterococci," FEMS Microbiology Letters, vol. 207, No. 2, Jan. 1, 2002, pp. 133-139.
G. Yu-Long, et al., "Effects of high hydrostatic pressure on energy metabolism of *Lactobacillus plantarum*," Database Biosis (online), vol. 46, No. 1, Feb. 2006, pp. 68-73, abstract XP002439577.
R. Chan, et al., "Construction and use of a computerized DNA fingerprint databese for lactic acid bacteria from silage," Journal of Microbiological Methods, vol. 55, Jan. 1, 2003, pp. 565-557.
Hashimoto et al., "Molecular identification of an a-L-rhamnosidase from *Bacillus* sp. strain GLI as an enzyme involved in complete metabolism of gellan", Biochemistry and Biophysics 415 (2003) 235-244 XP004432083.
Yadav et al., "Secretion of a-L-Rhamnosidase by *Aspergillus terreus* and Its Role in Debittering of Orange Juice", Journal of Scientific & Industrial Research vol. 39, Dec. 2000, pp. 1032-1037.
Cui et al., "Crystallization and preliminary crystallographic analysis of the family GH78 a-L-rhamnosidase RhaB from *Bacillus* sp, GL1", Acta Cryst. (2006)646-648 XP002551177.
Hashimoto et al., "Characterization of a-L-Rhamnosidase of*Baccillus* sp. GL1 Responsible for the Complete Depolymerization of Gellan", Archives of Biochemistry and Biophysics, vol. 368, No. 1, Aug. 1, pp. 56-60 1999 XP-002551176.
Nielsen, et al., "Bioavailability is Improved by Enymatic Modification of the Citrus Flavonoid Hesperidin in Humans: A Randomized, Double-Blind, Crossover Trial," The Journal of Nutrition, vol. 136, No. 2, Feb. 2006, pp. 404-408.

* cited by examiner

*Primary Examiner* — Kade Ariani
(74) *Attorney, Agent, or Firm* — K&L Gates LLP

(57) ABSTRACT

The present invention relates to methods for a long-term and sustained release of flavonoids, in particular rhamnose-containing flavonoids, and for prolonging the uptake of said flavonoids in the gastro-intestinal tract. It further relates to compositions comprising said flavonoid and α-rhamnosidase. It also encompasses compositions comprising hesperidin and hesperetin-7-glucoside.

12 Claims, 5 Drawing Sheets

LONG-LASTING ABSORPTION OF FLAVONOIDS

CROSS REFERENCE TO RELATED APPLICATIONS

The present application is a National Stage of International Application No. PCT/EP2007/007394, filed on Aug. 22, 2007, which claims priority to European Patent Application No. 06017678.1, filed on Aug. 24, 2006, the entire contents of which are being incorporated herein by reference.

FIELD OF THE INVENTION

The present invention relates to methods for a long-term and sustained release of flavonoids, in particular rhamnose-containing flavonoids, and for prolonging the uptake of said flavonoids in the gastro-intestinal tract. It further relates to compositions comprising said flavonoid and α-rhamnosidase. It also encompasses compositions comprising hesperidin and hesperetin-7-glucoside.

BACKGROUND ART

Flavonoids, or bioflavonoids, are a ubiquitous group of polyphenolic substances which are present in most plants, concentrating in seeds, fruit skin or peel, bark, and flowers. A great number of plant medicines contain flavonoids, which have been reported by many authors as having antibacterial, antioxidant, anti-inflammatory, antiallergic, antimutagenic, antiviral, antineoplastic, anti-thrombotic, and vasodilatory actions.

Recent developments described in WO 2005/058255 A1 also show the benefits of flavanone-containing compositions for improving the skin, hair and coat health of humans or pets.

In nature, these compounds mainly occur as glycosides. This conjugation with sugars impacts markedly their kinetics of absorption. For instance, flavonoid glucosides have a fast and early absorption while flavonoid rutinosides (rhamnose-glucoside) have a slow and late absorption.

For flavonoid rutinosides such as hesperidin, bioavailability is low and late in mammals due to the lack of the enzyme α-rhamnosidase in the small intestine, which would remove the rhamnose moiety of said flavonoid rutinosides. This leads to time-consuming progression of flavonoid rutinosides in the gastro-intestinal tract through to the colon.

Health foods and drinks containing long-acting flavonoid glycosides are described in JP 2003-073279 whereby a mixture of flavonoids having various degrees of glycosylation is included in the food product such that the absorption occurs throughout the gastro-intestinal tract.

JP 2000-078955 also describes a way to improve the absorption of flavonoids in food or medicine by providing a mixture of physiologically active flavonoids and derivatives thereof.

Further, Espin J. C. et al. describe in the Journal of Agricultural and Food Chemistry, 2004, 52(20), p. 6136-6142, the production of bioavailable glucoside flavonoids in fruit juices and green tea. This is achieved by treating the fruit juices and green tea with rhamnosidase enzymes from *Aspergillus aculeatus*.

OBJECT OF THE INVENTION

There thus still remains a need to provide alternative ways by which flavonoid compositions have a controlled effect in mammals.

SUMMARY OF THE INVENTION

Accordingly, this need is solved by the features of the independent claims. The dependent claims further develop the central idea of the invention.

Thus, in a first aspect of the invention, a composition comprising at least one rhamnose-containing flavonoid and α-rhamnosidase.

The compositions of the invention are formulated for cosmetic, nutritional and pharmaceutical use.

In a second aspect, the invention relates to a bacterium having α-rhamnosidase activity, which is selected from *Lactobacillus crispatus, Lactobacillus plantarum, Lactobacillus gasseri, Lactobacillus acidophilus* or *Leuconostoc mesenteroides*.

The present invention relates, in a further aspect, to the use of α-rhamnosidase in the preparation of a composition comprising at least one rhamnose-containing flavonoid for improving the bioefficacy and/or bioavailability of said flavonoid.

Under another aspect of the invention, the use of α-rhamnosidase and at least one rhamnose-containing flavonoid in the manufacture of a composition for the improvement of skin health is provided.

Also, the cosmetic use of the compositions of the invention represents another facet of the invention.

Also relating to the invention is a method for sustaining and/or improving the bioavailability of rhamnose-containing flavonoids comprising the step of providing a composition comprising at least one rhamnose-containing flavonoid and α-rhamnosidase, said α-rhamnosidase being in a state in which it is essentially not able to cleave the rhamnose moiety of said flavonoid.

A method for prolonging the plasma levels of metabolites of rhamnose-containing flavonoids after ingestion of said flavonoid comprising the step of orally providing a composition comprising at least one rhamnose-containing flavonoid and α-rhamnosidase, said α-rhamnosidase being in a state in which it is essentially not able to cleave the rhamnose moiety of said flavonoid, is a further aspect of the present invention.

A method for improving skin health comprising the step of orally administering a composition comprising at least one rhamnose-containing flavonoid and α-rhamnosidase, or orally administering separately and simultaneously a composition comprising at least one rhamnose-containing flavonoid and α-rhamnosidase, said α-rhamnosidase being in a state in which it is essentially not able to cleave the rhamnose moiety of said flavanoid, also falls under an aspect of the present invention.

Finally, the present invention encompasses compositions which comprise a mix of hesperidin and hesperetin-7-glucoside, preferably in a ratio of between 70/30 to 50/50.

FIGURES

The present invention is further described hereinafter with reference to some of its embodiments shown in the accompanying drawings in which.

Figure 8:
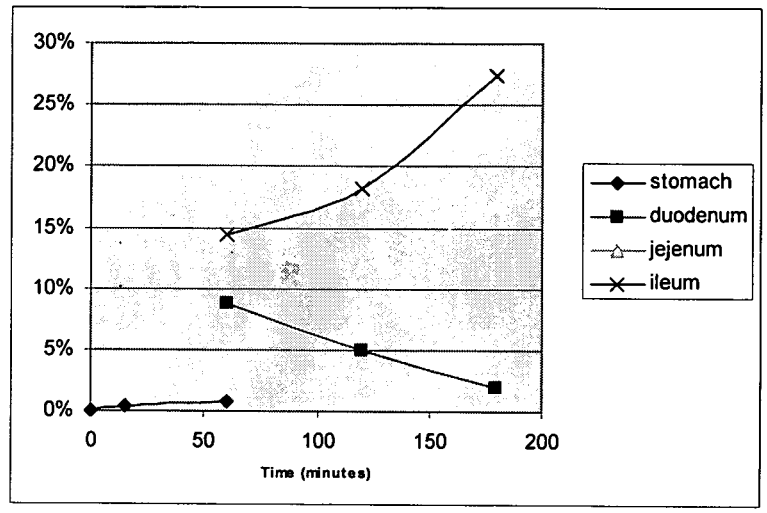

FIG. 8 illustrates the result of TIM1 experiment. Hydrolysis of hesperidin into hesperetin-7-glucoside monitored up to 3 hours in stomach and small intestine when using bacterial strains of *Lactobacillus gasseri* (CNCM I-3795). The figure shows that bacterial enzymes are poorly active in the stomach, only in the small intestine and that the amount of hydrolysed hesperidin decreases as the compounds moves down the GI-tract.

Figure 9:
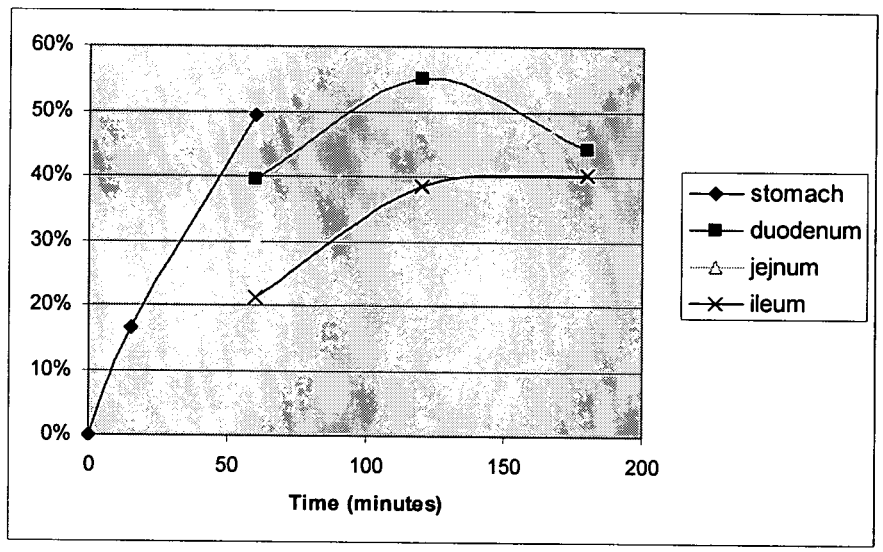

FIG. 9 illustrates the degree of hydrolysis of hesperidin into hesperetin-7-glucoside when using pure α-rhamnosidase enzyme. This graph shows that pure enzyme is active in stomach but less active in the GI-tract.

DETAILED DESCRIPTION OF THE INVENTION

The present invention relates to ways in which to control the absorption of rhamnose-containing flavonoids in mammals such that, after ingestion of said flavonoid, the absorption occurs equally at the upper and lower gastro-intestinal tract or throughout the length of the gastro-intestinal tract.

Thus, the basic principle underlying the present invention, in order to achieve a long-lasting and regulated effect, is a way to provide, in a regulated fashion, a flavonoid which is, at least partially, in an absorbable form throughout its passage in the gastro-intestinal tract of a mammal. Typically, the flavonoid is at least partially hydrolysed in the upper gastro-intestinal tract and also in the colon.

According to the invention, the presence of α-rhamnosidase at an early stage of digestion (stomach, small intestine) allows, to a certain extent, partial cleavage of rhamnose-containing flavonoids (cf. FIGS. 3-9). This results in the flavonoids being more absorbable, earlier on in the digestion process. Moreover, enzymes naturally present in the colon further the cleavage process such that a sustained absorption of flavonoids throughout their passage in the gastro-intestinal tract ensues.

Accordingly, the present invention proposes compositions comprising at least one rhamnose-containing flavonoid and an α-rhamnosidase, wherein the α-rhamnosidase is in a state in which it is essentially not able to cleave the rhamnose-containing flavonoid.

Provided the right conditions are met (environment, pH, temperatures etc.), α-rhamnosidase enzymes normally have the ability to cleave substrates comprising a rhamnose moiety.

In the compositions of the invention however, the enzyme is in a state such that it is essentially prevented from carrying out its normal function. It is only upon ingestion of the compositions that the environment of the enzyme is changed such that the new conditions (pH, temperature etc.) allow the enzyme to become active and thus to cleave the rhamnose moiety of the flavonoid.

Thus, in the compositions, uses or methods of the present invention, the α-rhamnosidase is in a state in which it is essentially not able to cleave the rhamnose-containing flavonoid. Only upon ingestion of the composition is the α-rhamnosidase able to cleave the rhamnose-containing flavonoid.

This "retarded" α-rhamnosidase activity ensures that the cleaving of the flavonoid by the α-rhamnosidase will only occur upon ingestion. Thus, only in gastro-intestinal tract conditions does the α-rhamnosidase activity occur.

This can be achieved by several means, according to varying embodiments of the invention.

For instance, this can be achieved by having the α-rhamnosidase in the composition under conditions in which it is "inactive", i.e. it is not able to cleave the rhamnose moiety of the flavonoid. An inactive α-rhamnosidase is, for example, an α-rhamnosidase which has been treated with an inhibitor, such that only when the conditions of the gastro-intestinal tract are met, the α-rhamnosidase is able to be active.

Alternatively, the conditions in the composition may be such that the enzyme is "inactive", for example by having high pH value. Upon ingestion, the low pH of the gastro-intestinal tract will provide favourable conditions for the α-rhamnosidase to become active.

According to another embodiment, this can be achieved by separating the α-rhamnosidase in the composition from the flavonoid. The separation is such that the α-rhamnosidase is not in direct contact with the flavonoid.

The separation can be made, for instance, by encapsulating α-rhamnosidase by means known in the art. Thus, the enzyme may be encapsulated such that it is only released under gastro-intestinal tract conditions.

Alternatively, by encapsulating the α-rhamnosidase in a micro-organism capable of releasing α-rhamnosidase, the α-rhamnosidase is not in direct contact with the flavonoid in the composition. Such "bio-encapsulation" may be achieved by an α-rhamnosidase producing strain of a micro-organism which is kept under conditions (water activity etc.) such that the micro-organism presents a low or zero metabolic rate. The conditions (water activity etc.) in the composition are therefore such that the micro-organism is not releasing the enzyme under these conditions. The α-rhamnosidase is "bio-encapsulated" within or on the outside of the cell walls of the micro-organism.

Thus, in the present invention, by "α-rhamnosidase in a state in which it is essentially not able to cleave the rhamnose moiety of the rhamnose-containing flavonoid" is meant any form of the enzyme as described above.

When an α-rhamnosidase-producing micro-organism is used in the compositions or the methods of the present invention, it is preferably a bacterium. More preferably, the micro-organism is selected from *Lactobacillus, Bifidobacterium, Streptococcus, Lactococcus, Enterococcus, Bacillus, Staphylococcus, Leuconostoc, Pediococcus, Oenococcus* etc.

Most preferably, the micro-organism is selected from *Lactobacillus crispatus* (ATCC 33820), *Lactobacillus crispatus*

(CNCM I-3654), *Lactobacillus plantarum* (ATCC 8014), *Lactobacillus plantarum* (CNCM I-3653), *Lactobacillus gasseri* (CNCM I-3795) or mixtures thereof.

Thus, a micro-organism having α-rhamnosidase activity selected from *Lactobacillus crispatus* (ATCC 33820), *Lactobacillus crispatus* (CNCM I-3654), *Lactobacillus plantarum* (ATCC 8014), *Lactobacillus plantarum* (CNCM I-3653) or *Lactobacillus gasseri* (CNCM I-3795) is part of the present invention.

*Lactobacillus gasseri* CNCM I-3795 was deposited on Aug. 17, 2007 under the Budapest treaty with the Collection Nationale de Cultures de Microorganism, Institut Pasteur, 25, Rue du Docteur Roux, F-76724 Paris Cedex 15.

The micro-organism is preferably present in the compositions of the invention in an amount of $10^6$-$10^{10}$ cfu/g. More preferably it is present in an amount of $10^9$ cfu/g.

The micro-organism capable of producing α-rhamnosidase may further be encapsulated. Encapsulation of microorganisms is a method well-known to the person of skill in the art.

Figure 1A:
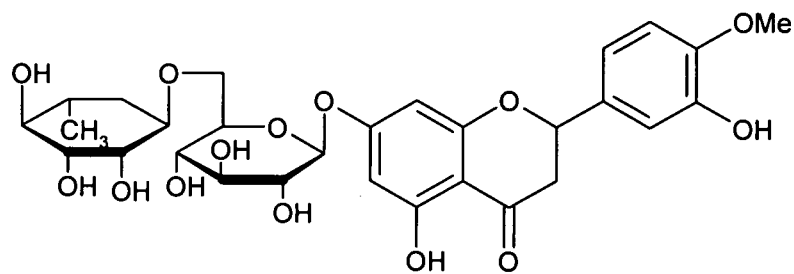
FIG. 1a depicts the molecular structure of hesperidin.

The flavonoids used in the present invention may be selected from any flavonoid comprising a rhamnose moiety. Any such rhamnose-containing flavonoid may be selected from the group consisting of hesperidin, rutin, eriotricin, naringin, neohesperidin, diosmin, linarin, poncirin, prunin, etc. and any possible combination from this list comprising two or more components from the list. Preferably, the flavonoid is hesperidin (FIG. 1a).

Figure 1B:
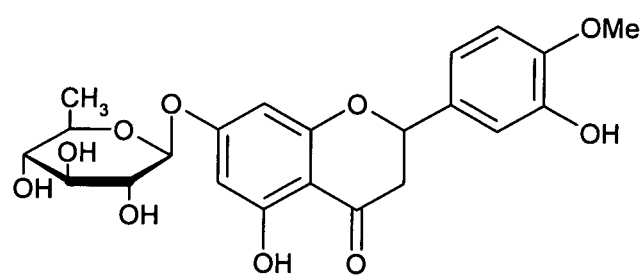
FIG. 1b depicts the molecular structure of hesperetin-7-glucoside.
Figure 1C:
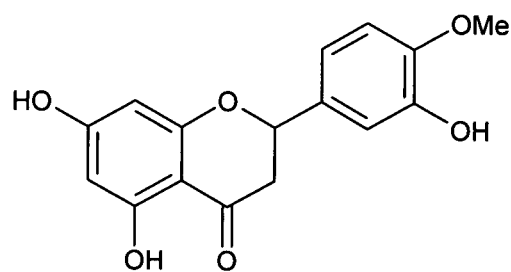
FIG. 1c depicts the molecular structure of hesperetin.

Hesperidin (FIG. 1a) comprises a rutinose (rhamnose-glucose) moiety. In the presence of an active α-rhamnosidase enzyme, the rhamnose moiety of hesperidin may be cleaved off to a certain extent to yield hesperetin-7-glucoside (FIG. 1b). In turn, hesperetin-7-glucoside may be further cleaved by other enzymes, e.g. glucosidase enzymes which are present in the gastro-intestinal tract, to give hesperetin (FIG. 1c).

Figure 2:
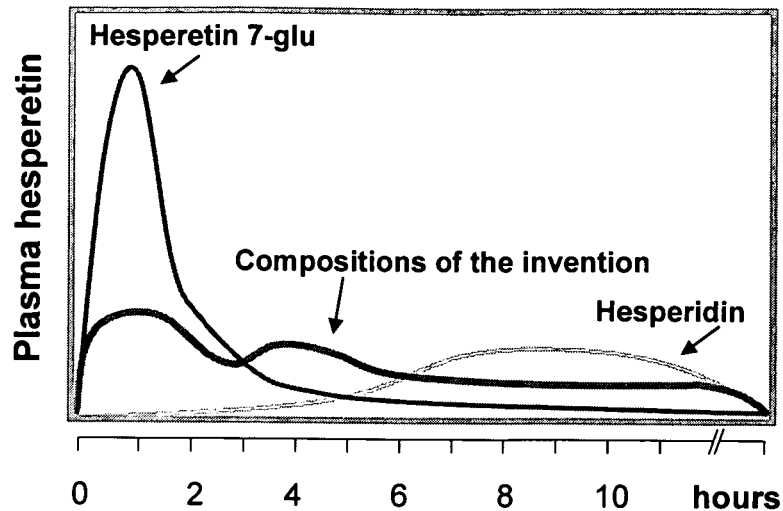
FIG. 2 is a graph comparing the plasma hesperetin levels depending on whether hesperetin-7-glucoside alone is ingested, whether hesperidin alone is ingested or whether a composition according to the present invention is consumed.
Figure 3:
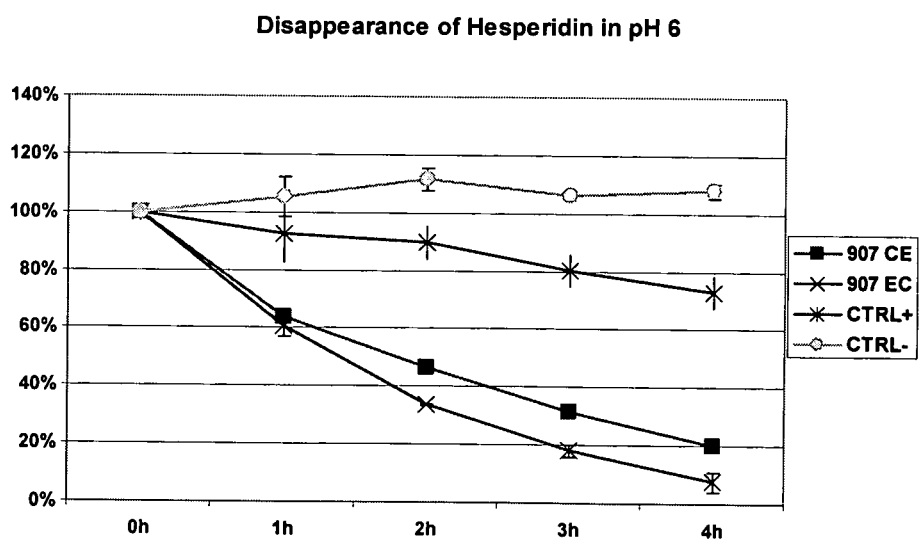
FIG. 3 shows the disappearance of hesperidin in vitro in conditions close to those of the small intestine (pH 6) in the presence of pure α-rhamnosidase (CTRL+), in the presence of entire cells of *Lactobacillus gasseri* CNCM I-3795 (907 EC), in the presence of broken cells of *Lactobacillus gasseri* CNCM I-3795 (907 CE) or in the absence of any bacteria/enzyme (CTRL−).
Figure 4:
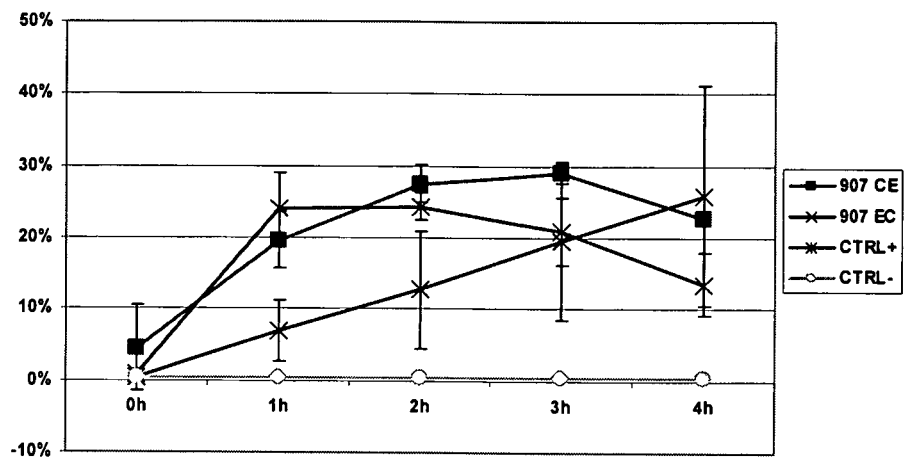
FIG. 4 shows the formation of hesperetin-7-glucoside at pH 6 (calculated from the starting point amount of hesperidin (100%)), wherein CTRL+, CTRL−, 907 CE and 907 EC have the same meaning as in FIG. 3.
Figure 5:
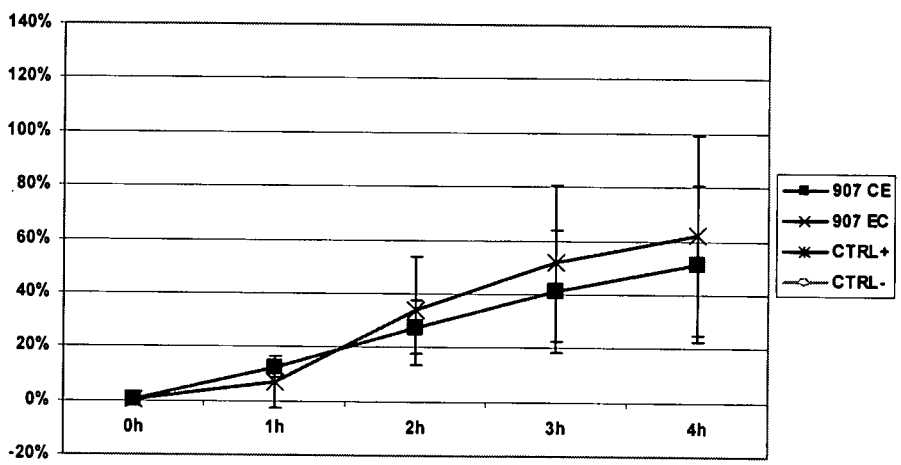
FIG. 5 shows the formation of hesperetin at pH 6 when treating hesperidin with entire or broken cells of *Lactobacillus gasseri* (CNCM I-3795)
Figure 6:
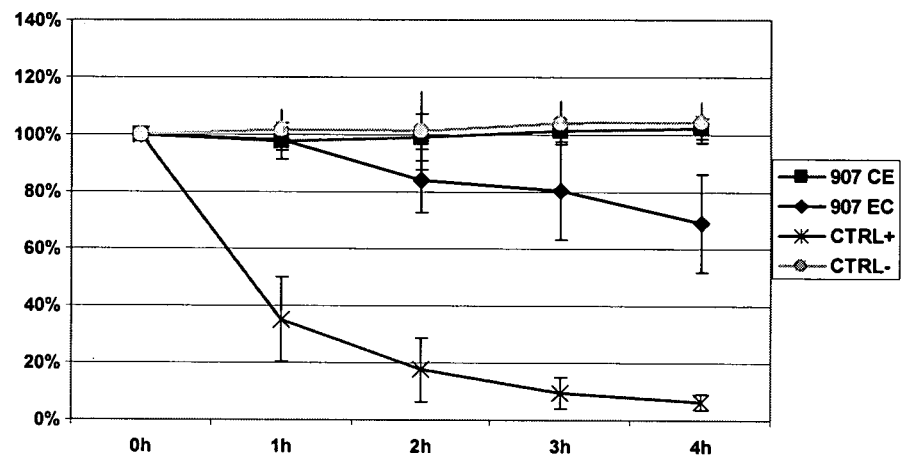
FIG. 6 shows the disappearance of hesperidin in vitro in conditions close to those of the stomach after digestion of a meal (pH 4) in the presence of pure α-rhamnosidase (CTRL+), in the presence of entire cells of *Lactobacillus gasseri* CNCM I-3795 (907 EC), in the presence of broken cells of *Lactobacillus gasseri* CNCM I-3795 (907 CE) or in the absence of any bacteria/enzyme (CTRL−).
Figure 7:
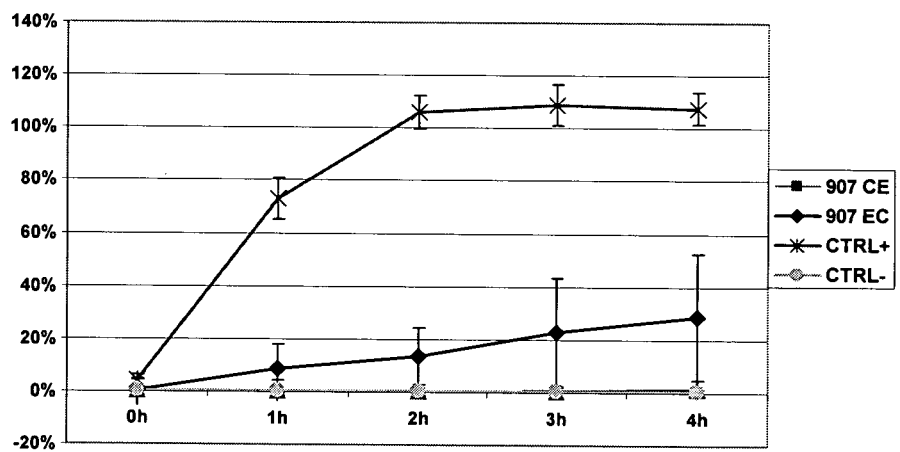
FIG. 7 shows the formation of hesperetin-7-glucoside at pH 4 (calculated from the starting point amount of hesperidin (100%)), wherein CTRL+, CTRL−, 907 CE and 907 EC have the same meaning as in FIG. 6.

Referring to FIG. 2, it can be seen that, on one hand, the plasma level of hesperetin (FIG. 1c) upon ingestion of hesperetin-7-glucose (FIG. 1b) shows a sharp peak shortly after ingestion. Without wishing to be bound by theory, it is thought that this is due to the presence of enzymes which are able to cleave the glucose moiety off, such that hesperetin is readily absorbable.

On the other hand, the hesperetin plasma level resulting from the ingestion of hesperidin (FIG. 1a) appears only later and to a smaller extent. Without wishing to be bound by theory, it is thought that this is due to the presence of enzymes able to cleave the rutinose moiety of hesperidin only at a later stage of passage through the gastro-intestinal tract.

Thus, the compositions of the present invention advantageously provide a plasma level of hesperetin which is sustained over a longer period of time (cf. FIG. 2).

Further, according to another embodiment of the present invention, such a sustained plasma level of hesperetin is also provided by compositions comprising a mix of hesperidin (FIG. 1a) and hesperetin-7-glucoside (FIG. 1b). Preferably, these are present in the compositions in a ratio of hesperidin to hesperetin-7-glucoside of between 70/30 to 50/50.

The amount of flavonoid in the compositions of the present invention is such that it corresponds to an amount ranging from 0.01 mg to 1 g of the aglycone equivalent of the flavonoid compound. Preferably, the flavonoid is present in an amount ranging from 10 mg to 800 mg of the aglycone equivalent of the flavonoid compound.

For instance, when hesperidin (FIG. 1a) is used in a composition of the present invention, it is present in an amount which will provide 0.01 mg to 1 g, preferably 10 mg to 800 mg of the corresponding hesperetin (FIG. 1c). This is easily calculated by a man of skill in the art.

In the compositions of the present invention, the α-rhamnosidase may be present in an amount sufficient to provide between 10-50% of the flavonoid aglycone or of a form of glycosylated flavanoid which is absorbable at the early stages of digestion.

For instance, in the case where the flavanoid is hesperidin, the amount of α-rhamnosidase used is an amount sufficient to provide between 10-50% of hesperetin 7-glucoside (FIG. 1b) or hesperetin (FIG. 1c) in the upper gastro-intestinal tract (small intestine). This can be easily assessed by methods known in the art, such as experiments with TIM-1 of TNO and in vivo confirmation (cf. FIGS. 8 and 9).

The compositions of the present invention are preferably formulated for use as nutritional, pharmaceutical or cosmetic compositions.

Therefore, the compositions of the present invention may be dry, moist, or semi-moist compositions. By "dry", is meant compositions having a water activity below 0.6. By "semi-moist" is meant compositions having a water activity between 0.6 and 0.9 and by "moist" is meant composition having a water activity above 0.9.

They may be selected from liquid, dry or semi-dry compositions such as solutions, sprays, powders, tablets, capsules, yoghurt, biscuit, milk, beverages, chocolate, ice cream, breakfast cereal flakes or bars, milk powders, soy-based products, non-milk fermented products, nutritional supplements, food supplement, pet food, infant formula etc.

For ingestion, many embodiments of oral compositions and in particular of food supplements are possible. They are formulated by means of the usual methods for producing sugar-coated tablets, gelatine capsules, gels, emulsions, tablets, capsules or solutions. In particular, the rhamnose-containing flavonoids and the α-rhamnosidase or, in a different embodiment, the hesperidin and hesperetin-7-glucoside may be incorporated into any other forms of food supplements or of enriched foods, for example food bars, or compacted or non-compacted powders. The powders can be diluted with water, in a fizzy drink, dairy products or soya-derived products or can be incorporated into food bars.

The compositions may comprise the usual excipients and constituents, e.g. fatty and/or aqueous constituents, humectifying agents, thickeners, preserving agents, texturing, flavouring and/or coating agents, antioxidants, dyes that are usual in the food domain.

According to a further aspect of the present invention, α-rhamnosidase may be used in the preparation of a composition comprising at least one rhamnose-containing flavonoid and wherein the α-rhamnosidase is in a state in which it is essentially not able to cleave the rhamnose moiety of said flavonoid, for improving the bioefficacy and/or bioavailability of said flavonoid. By "composition" is covered any composition according to the invention as described above.

Bioefficacy is defined as the proportion of the ingested nutrient converted to an active form of the nutrient having significant biological effect. It is closely related to bioavailability which is defined as the degree to which a substance is absorbed into the systemic circulation. By improving the bioefficacy and/or bioavailability of a flavonoid, the present invention offers the advantage of a more effective composition with more durable and sustained effects.

Thus, the present invention also provides a method for sustaining and/or improving the bioavailability of rhamnose-containing flavonoids comprising the step of providing a composition comprising at least one rhamnose-containing flavonoid and α-rhamnosidase, said α-rhamnosidase being in a state in which it is essentially not able to cleave the rhamnose moiety of said flavonoid.

A comparison of the plasma levels after ingestion of hesperidin (FIG. 1a) or after ingestion of hesperetin-7-glucoside (FIG. 1c) shows a noticeable difference to the compositions of the present invention. Indeed, after the ingestion of the compositions of the present invention, the hesperetin plasma levels are maintained for a sustained period of time (FIG. 2).

Thus, the present invention further encompasses a method for prolonging the plasma levels of metabolites of rhamnose-containing flavonoids after ingestion of said flavonoid comprising the step of orally providing a composition comprising at least one rhamnose-containing flavonoid and α-rhamnosidase, said α-rhamnosidase being in a state in which it is essentially not able to cleave the rhamnose moiety of said flavonoid.

In the methods of the present invention, the α-rhamnosidase may be provided separately from the composition comprising the rhamnose-containing flavonoid. For example, said α-rhamnosidase may be provided as a tablet, capsule etc. to be ingested at the same time as the composition comprising the flavonoid. Alternatively, it may be provided, for example, as a powder to be sprinkled onto the flavonoid-containing composition. The skilled person could readily envisage a variety of different alternatives to the specific embodiments mentioned herein.

Under another aspect, the compositions according to the present invention may be used cosmetically. By "cosmetic use" is meant a non-therapeutic use which may improve the aesthetic aspect or comfort of the skin, coat and/or hair of humans or pets.

In this context, the cosmetic use may include preventing damages to, and/or improving the skin, coat and/or hair of humans or pets. Such damages include in particular actinic and ageing damages of the skin such as dryness, irregular pigmentation (notably freckling, lentigines, guttate hypomelanosis and persistent hyperpigmentation), wrinkling (notably fine surface lines and deep furrows), stellate pseudoscars, elastosis, inelasticity, telangiectasia, venous lakes, comedones, sebaceous hyperplasia, acrochordon and seborrhea keratosis.

The cosmetic use may also have particular benefits on hair and coat, such as an improved hair or coat density, fibre diameter, colour, oiliness, glossiness, sebum production and may help to prevent hair or coat loss.

The present invention further encompasses therapeutic uses such as dermatological uses for instance. Indeed, the use of α-rhamnosidase and at least one rhamnose-containing flavonoid, wherein the α-rhamnosidase is in a state in which it is essentially not able to cleave said flavonoid, in the manufacture of compositions for the improvement of skin health, falls under another aspect of the invention. Said compositions may also be used for the prevention of inflammation or for the improvement of bone and/or cardiovascular health. By "composition" is covered any composition according to the invention as described above.

Under this embodiment, the compositions according to the present invention may be utilised for treating and/or preventing damages of the skin which are, for example, produced by a stress situation e.g. by means of a chemical, biological or a physical stress, e.g. by exposure to oxidants or carcinogens, exposure to bacteria, viruses, fungi, lipids derived from surrounding cells and/or microbes, or exposure to UV-irradiation.

These damages further comprise actinic keratoses, purpura, cherry angiodema, basal cell carcinoma and squamous cell carcinoma, skin burning and/or blistering, epidermal hyperplasia, inflammation, immune suppression, and cancer, e.g. non-melanoma and melanoma skin cancers.

The effect of the compositions according to the present invention, on skin of humans or pets, can be measured by using conventional methods including minimal erythemal dose (MED), colorimetry, transepidermal water loss, DNA repair, measure of interleukins and proteoglycans production, or collagenase activity, barrier function or cell renewal.

Consequently, a method for improving skin health comprising the step of orally administering a composition comprising at least one rhamnose-containing flavonoid and α-rhamnosidase, or orally administering separately and simultaneously a composition comprising at least one rhamnose-containing flavonoid and α-rhamnosidase, said α-rhamnosidase being in a state in which it is essentially not able to cleave the rhamnose moiety of said flavonoid, also falls under an aspect of the present invention. This method is also useful in improving cardiovascular and bone health.

It will be understood that the concept of the present invention may likewise be applied as an adjuvant therapy assisting in presently used medications. Since the compositions of the present invention may easily be orally administered with food material, special clinical food may be administered containing a high amount of the objective substances.

Furthermore, the concept of the present invention may likewise be extended to topical applications of compositions comprising a rhamnose-containing flavonoid and an alpha-rhamnosidase enzyme.

The present invention is further illustrated by means of the non-limiting examples described below.

EXAMPLES

Example 1

Materials

Hesperidinase "Amano" Conc. (A.MANO PHARMACEUTICAL CO., LTD.)

Cleavage of Hesperidin by Bacterial Crude Extracts In Vitro

To test if the bacterial alpha-rhamnosidases can recognise and cleave hesperidin as a substrate, the crude extracts of the cells grown in the presence of rhamnose are incubated with hesperidin at pH 4 and pH 6 for 4 hours and 8 hours and the analysis is done by HPLC. The results are presented in the table below as a percentage of hesperidin or its derivatives based on the total hesperidin amounts at the beginning of the reaction (0.08 mg/mL). The tests were performed with 0.08 mg hesperidin/mL, which is an approximate concentration of hesperidin aimed for the final product and crude extracts of $3 \times 10^9$ bacteria/mL.

The results show that the two strains have both α-rhamnosidase and β-glucosidase activity and as a consequence cleave hesperidin into hesperetin-7-glucoside and aglycone to different extents, depending on the reaction conditions. The results suggest that bacteria can be used for partial hesperidin transformation into hesperetin-7-glucoside and aglycone in situ.

| % | | Bacterial counts | Hesperidin 4 h | 8 h | Hesperetin-7-glucoside 4 h | 8 h | aglycone 4 h | 8 h |
|---|---|---|---|---|---|---|---|---|
| Control (−) (no enzyme) | pH 4 | — | nd | 95 | nd | 0 | nd | 0 |
|  | pH 6 |  | nd | 95 | nd | 0 | nd | 0 |
| Control (+) pH4 (hesperedinase) | pH 4 | — | 0 | 0 | 92 | 93 | 0 | 0 |
| pH6 | pH 6 |  | 66 | 49 | 25 | 40 | 0 | 0 |
| L. acidophilus NCC 3010 | pH 4 | $3.4 \times 10^9$/ml | 18 | 5 | 28 | 18 | 26 | 42 |
|  | pH 6 |  | 26 | 10 | 6 | 5 | 13 | 27 |
| L. plantarum NCC1313 | pH 4 | $3.4 \times 10^9$/ml | 12 | 8 | 5 | 4 | 62 | 66 |
|  | pH 6 |  | 9 | 0 | 5 | 0 | 25 | 33 |

Nd: not determined

Example 2

0.2 to 50 mg of hesperidin/g of product is mixed with $10^7$-$10^{10}$ cfu/(g of product) of alpha-rhamnosidase active bacteria. The resulting mixture is blended with a suitable carrier. Carriers may be selected from fermented milk, yogurt, fresh cheese, renneted milk, confectionery bar, breakfast cereal flakes or bars, drink, milk powder, soy-based product, non-milk fermented product.

The invention claimed is:

1. A composition comprising at least one rhamnose-containing flavonoid and an α-rhamnosidase, and the α-rhamnosidase is not in direct contact with the flavonoid, the α-rhamnosidase is encapsulated in a micro-organism capable of producing α-rhamnosidase, the micro-organism selected from the group consisting of *Lactobacillus crispatus* ATCC33820, *Lactobacillus crispatus* CNCM I-3654, *Lactobacillus plantarum* ATCC8014, *Lactobacillus plantarum* CNCM I-3653, *Lactobacillus gasseri* CNCM I-3795 and mixtures thereof.

2. The composition according to claim 1, wherein the micro-organism is present in an amount of $10^6$-$10^{10}$ cfu/g.

3. The composition according to claim 1, wherein the micro-organism capable of producing a-rhamnosidase is encapsulated.

4. The composition according to claim 1, wherein the flavonoid is hesperidin.

5. The composition according to claim 4, wherein the α-rhamnosidase is present in an amount sufficient to provide between 10-50% of hesperetin 7-glucoside or hesperetin in the upper gastro-intestinal tract.

6. The composition according to claim 1 wherein the rhamnose-containing flavonoid is present in an amount corresponding to 0.01 mg to 1 g of the aglycone equivalent of the flavonoid compound.

7. The composition according to claim 6, wherein the rhamnose-containing flavonoid is present in an amount corresponding to 10 mg to 800 mg of the aglycone equivalent of the flavonoid compound.

8. The composition according to claim 1, wherein the composition is formulated as a nutritional, pharmaceutical or cosmetic composition.

9. The composition according to any of the preceding claims, which is selected from liquid, solutions, sprays, powders, tablets, capsules, yoghurt, biscuit, milk, beverages, chocolate, ice cream, breakfast cereal flakes or bars, milk powders, soy-based products, non-milk fermented products, nutritional supplements, food supplement, pet food, infant formula and combinations thereof.

10. A method of improving aesthetics or comfort of skin, a coat, or hair of humans or pets, the method comprising the step of orally administering a composition according to claim 1 to a human or a pet in need of same.

11. A method of treating damages to the skin, coat and/or hair of humans or pets, the method comprising the step of orally administering the composition of claim 1 to a human or a pet in need of same.

12. The composition according to claim 1, wherein the micro-organism is present in an amount of $10^9$ cfu/g.

* * * * *